(12) United States Patent
Cohn et al.

(10) Patent No.: US 7,339,660 B1
(45) Date of Patent: Mar. 4, 2008

(54) ILLUMINATION DEVICE FOR PRODUCT EXAMINATION

(75) Inventors: Avi P. Cohn, Hood River, OR (US); Larry H. Mack, Jr., Sugar Land, TX (US)

(73) Assignee: Satake USA, Inc., Stafford, TX (US)

( * ) Notice: Subject to any disclaimer, the term of this patent is extended or adjusted under 35 U.S.C. 154(b) by 0 days.

(21) Appl. No.: 11/564,622

(22) Filed: Nov. 29, 2006

(51) Int. Cl.
*G01N 21/00* (2006.01)
*G01J 3/50* (2006.01)
*B07C 5/342* (2006.01)

(52) U.S. Cl. .................. 356/237.1; 250/226; 209/581; 209/582; 382/110

(58) Field of Classification Search .. 356/237.1–237.3, 356/399–401, 51–68; 250/221, 224, 226, 250/559.46; 209/580–582; 382/110; 362/231
See application file for complete search history.

(56) References Cited

U.S. PATENT DOCUMENTS

| | | | |
|---|---|---|---|
| 4,972,093 A | | 11/1990 | Cochran et al. |
| 5,451,773 A | * | 9/1995 | Triner et al. ............. 250/223 B |
| 5,508,512 A | | 4/1996 | Gray et al. |
| 5,522,512 A | * | 6/1996 | Archer et al. ............... 209/580 |
| 5,526,437 A | * | 6/1996 | West ........................... 382/141 |
| 5,539,485 A | * | 7/1996 | White ........................ 396/431 |
| 5,713,661 A | * | 2/1998 | White ......................... 362/355 |
| 5,751,833 A | * | 5/1998 | Blit et al. .................... 382/110 |
| 5,779,058 A | * | 7/1998 | Satake et al. ............... 209/581 |
| 5,822,053 A | | 10/1998 | Thrailkill |
| 5,917,927 A | * | 6/1999 | Satake et al. ............... 382/110 |
| 6,191,859 B1 | * | 2/2001 | Winterbottom et al. ..... 356/406 |
| 6,225,620 B1 | * | 5/2001 | Campbell et al. ........... 250/221 |
| 6,384,421 B1 | * | 5/2002 | Gochar, Jr. ............ 250/559.46 |
| 6,563,576 B2 | | 5/2003 | Gschweitl |
| 6,646,218 B1 | * | 11/2003 | Campbell et al. ........... 209/582 |

* cited by examiner

*Primary Examiner*—Sang H. Nguyen
(74) *Attorney, Agent, or Firm*—Crain, Caton & James, P.C.; James E. Hudson, III

(57) ABSTRACT

An illumination device for use with a product inspection machine inspecting products according to at least one characteristic. The invention also pertains to an illumination device for use in sorting machines that optically sort or separate nonstandard fungible objects from standard objects as they pass a viewing station by viewing such objects illuminated by at least one wavelength. The invention includes a plurality of arrays of semiconductor light sources impinging on passing product and at least one array of semiconductor light sources of wavelength and intensity equal to the plurality of arrays impinging on a background surface for detection and comparison.

11 Claims, 7 Drawing Sheets

ILLUMINATION DEVICE FOR PRODUCT EXAMINATION

CROSS REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

1. Field of the Invention

This invention relates generally to a product illumination device for examination of passing product wherein multiple wavelengths and intensities may be selected, and particularly for use in for product sorting.

2. Description of the Related Art

A typical sorting machine of the type with which the present invention is used is a high-speed sorting machine for use with small products, including fungible products in the food and pharmaceutical industries. As used herein, product refers not only to a manufactured good but also to component items from which production of a good may be accomplished. As a result, the invention may also be used in conveyor sorting machines, for sorting of other flowing materials, such as plastic pellets and ammunition, and for quality control examination of product.

For example, individual rice grains may be sorted in a gravity-fed sorter to separate grains selected as "substandard." In the art, "substandard" may apply to a grain having any undesirable characteristic, including color, shape, size or breakage, or any other characteristic not within the limits for acceptable products for a particular sorting. Alternative feed systems, such as belt driven conveyors, are also well-known in the art. Alternatively, certain rarer products may be desirable and therefore deflected from the flow of the less rare and less desirable remaining products. Likewise other materials may be sorted from the product flow, including, such as in the case of harvested goods, non-product materials such as glass, rocks, sticks and bran.

Sorting machines may employ two or more optical sensors to differentiate based on color hues, size, moisture content or other characteristics as determined in radiation bands, which may be outside the visible color spectrum. When such sorting is accomplished by use of two radiation bands, the sorting procedure is referred to as bichromatic sorting.

Optical sorting machines of the type generally described above employ optical sensors that include multiple photodetectors, such as a charged-couple device and photodiode arrays. The photodetectors are positioned to observe the illuminated product stream through a light-penetrating window. The product stream typically passes between an optical sensor and a background, where the background has a color shade that matches the product stream in standard color or shade so that only a variation in a product color or shade causes a detection event. The illumination is from one or more light sources directed at the product stream to cause standard reflectivity or transmission (transluminence) from standard products in the radiation bands being observed and to cause nonstandard reflectivity from nonstandard products in those bands.

One of the main components of such a sorting system is the illumination assembly. The illumination assembly provides a starting point for the reception quality of the vision system. Typically, the assembly is required to supply a uniform light supply and have a high intensity at the object point (sometimes referred to as the scan line) of the vision system. Most inspection systems include some sort of illuminator. Conventional illuminators include incandescent and fluorescent lamps and light emitting diodes. Various optical arrangements have been designed for better illumination, such as ringed lamp arrays, focused filament projectors, and fiber optic emitters. Uneven illumination in conventional illuminators may result in detection of shadows as defects. While the characteristics commonly measured incorporate illuminators including human-visible light sources, machine vision systems may measure energy waves outside the human vision range.

Such sorting machines also include one or more ejector mechanisms located downstream of the sensor or sensors with multiple nozzles associated with one or more valves actuated by an electrical signal coordinated with sensor detection. When a product having or lacking selected criteria is detected, an electrical signal is produced to actuate the valve of the ejector nozzle associated with the predicted location of the selected product at the predicted time the selected product will pass the ejector. The time elapsed between the selected product passing the sensor or sensors and the selected product being ejected is minimal to limit possible vertical and/or horizontal deflection of the selected product upon contact with non-selected products. Each ejector is therefore normally located as close as possible to the plane at which the optical sensor or sensors reviews the passing products, typically referred to as the scan line, ideally being just downstream therefrom and closely adjacent thereto.

It would be an improvement over the prior art to provide an illumination device that provides intense, consistent illumination of the products to be viewed along a linear or elongated scan line, thereby providing consistent identification of selected characteristics and substantially reducing mischaracterization of products as having occlusions or other defects actually caused by shadows.

The prior art typically utilizes quartz halogen or fluorescent lights as the main illumination source. To adjust the wavelength or wavelengths of light and the light intensity impinging on passing product, prior art teaches the use of filters, typically mounted adjacent the camera. The prior art is prone to waste energy as heat, rather than light, which must then be removed from the sorting machine. Moreover, the combining color band in a monochromatic application is limited.

In bi-chromatic sorters, a combination of red/green and red/blue filters is required to limit the wavelengths and/or intensity impinging on the product. Such a system requires significant disassembly, and therefore lost productivity, when any change to the wavelengths and/or intensity is desired. Such a change may be desired if a different product is to be sorted or if a different characteristic is selected for sorting.

Additionally, it would be an improvement to the prior art to provide an illumination device that may instantaneously adjust the wavelength or wavelengths and/or wavelength intensity impinging on passing product.

SUMMARY OF THE INVENTION

It is therefore, a principle object of the present invention to provide an illumination device that may instantaneously adjust both the wavelengths and intensity impinging on passing product.

The present invention comprises an illumination assembly for a machine vision viewer for a product sorting machine that provides a flow of objects along a horizontal scan line. The present invention includes a horizontally-disposed product illumination assembly with a plurality of sequenced semiconductor light sources, which may be light-emitting diodes, of one or more colors mounted thereon, and a corresponding horizontally-disposed background surface illuminated by a plurality of sequenced semiconductor light sources of one or more colors. Moreover, the intensity of any emitted color or colors may be adjusted to further vary the light color impinging on passing product and the corresponding background surface against which the product is imaged for sorting.

A passage exists between the product illumination assembly and the background assembly through which product to be sorted passes. A linear viewport, parallel to the horizontally-disposed product illumination assembly, is provided for one or more detectors to identify any product passing between the product illumination assembly and the background assembly having a characteristic found in a the minority of product. An ejector is positioned adjacent the illumination device.

In the preferred embodiment, a pair of product illumination assemblies are employed, wherein a background assembly is integrated into each product illumination assembly. The two product illumination assemblies are oriented in parallel such that a detector imaging through the linear viewport of the first product illumination assembly images the opposing background surface in the absence of product.

Use of semiconductor light sources of a plurality of colors provides advantages over the prior art. The need for replacement or alteration of color filters to obtain different wavelengths and intensities for characteristic selection is eliminated. Likewise, in monochromatic sorting systems, multiple colors may be used to enhance the color difference of the product having the characteristic to be deflected. On bi-chromatic applications, there is no need to add a color filter in front of the detector when using a simple dichroic mirror. Finally, each channel (semiconductor light source array) can be a combination of colors on bi-chromatic applications.

The height of each product illumination assembly is limited to the minimum size practicable to contain at least two rows of semiconductor light sources, a background surface of sufficient height, the illumination for the background surface, and sufficient depth for the light emitted from the semiconductor light sources on the product illumination assembly to converge and blend at the scan line and for the light from the semiconductor light sources illuminating the background surface to converge and blend on the background. The semiconductor light sources used to illuminate the product may be concurrently used to illuminate the background surface. Various methods to promote convergence and blending of the light of the semiconductor light sources, particularly light emitting diodes (LEDs), are well known in the art.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

So that the manner in which the described features, advantages and objects of the invention, as well as others which will become apparent, are attained and can be understood in detail, more particular description of the invention briefly summarized above may be had by reference to the embodiments thereof that are illustrated in the drawings, which drawings form a part of this specification. It is to be noted, however, that the appended drawings illustrate only a typical preferred embodiment of the invention and are therefore not to be considered limiting of its scope as the invention may admit to other equally effective embodiments.

DETAILED DESCRIPTION OF THE PREFERRED EMBODIMENT

Figure 2:
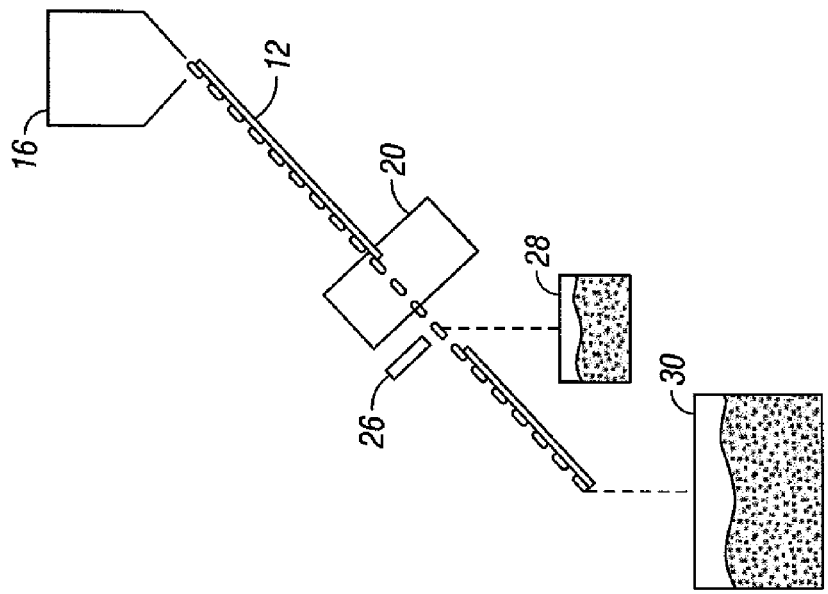
FIG. 2 depicts a simplified side view of a typical machine viewing system known in the art.
Figure 1:
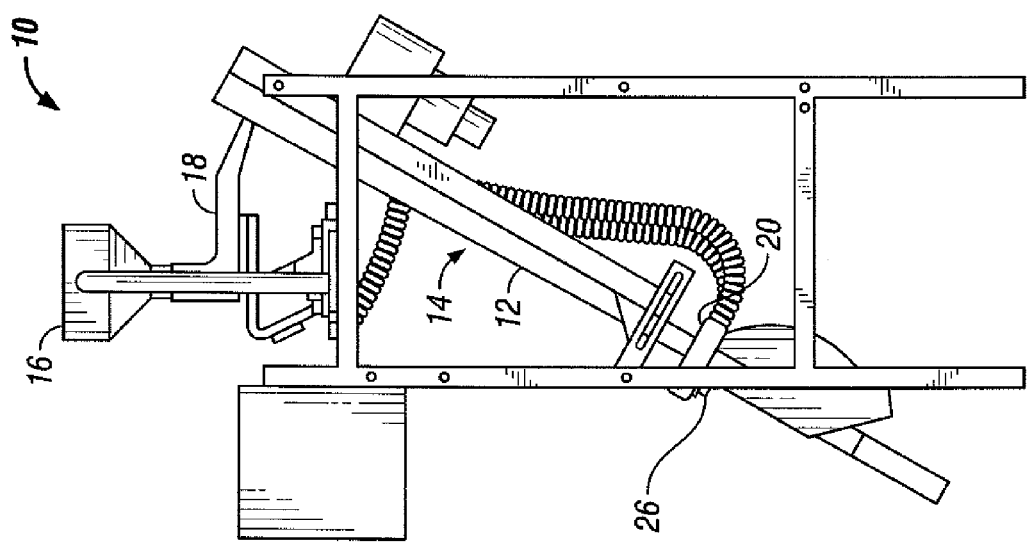
FIG. 1 depicts a side view of a typical sorting machine known in the art including the illumination device of the present invention.

Referring first to FIG. 1, a typical product-sorting machine including the illumination device of the present invention is depicted. The product-sorting machine 10 includes a hopper 16, a feeder 18, a slide 12, a vision system 20, and an ejector 26. The components of typical product sorting machine 10 are illustrated in FIG. 2, including a container 28 for segregated products and a bin 30.

The products to be viewed and sorted by the typical product-sorting machine 10 are retained in hopper 16 and are ultimately dispensed onto slide 12 by feeder 18. Feeder 18 may be of any type commonly known in the art, such as a conveyor or a vibratory feeder.

In the exemplary product-sorting machine 10, momentum is imparted to the product to be sorted by the product conveyor 14, which may be a gravity slide 12 or belt conveyor. Prior to the product passing before vision system 20, product conveyor ceases to support the product, directing the product along trajectory 32. The product sorting machine 10 of the embodiment disclosed in FIGS. 1 and 2 provides for free fall of the products past slide 12.

The product to be sorted may be any of a plurality of organic or inorganic objects, such as, for example, grains, nuts, and plastic pellets. The products may be viewed and sorted based on various criteria determined by the user, including size, color, defects and other characteristics.

Figure 3:
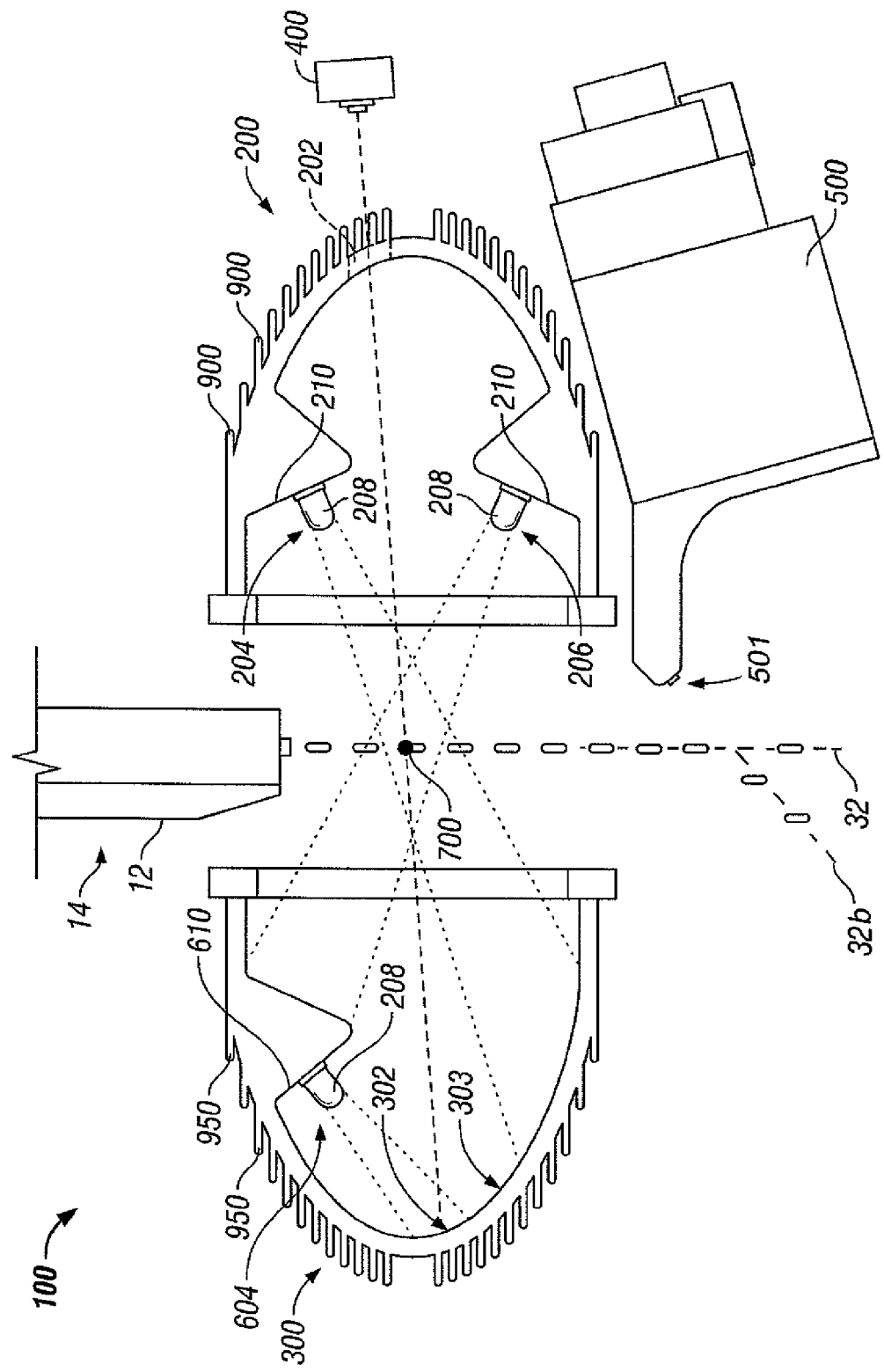
FIG. 3 depicts a cross-sectional view of the illumination device of the present invention.

Referring to FIG. 3, vision system 20 includes an illumination device 100 that is composed of a horizontally disposed product illumination assembly 200 and a corresponding horizontally-disposed background assembly 300, a detector 400, and an ejector 500. In free fall, the product passes the first, or upper edge, of illumination device 100 used in conjunction with vision system 20, and the second, or lower edge, of illumination device 100. In operation, as a continuous flow of product passes through product-sorting machine 10 and therefore past illumination device 100, illumination device 100 provides continuous and uninterrupted illumination of the flow of passing product. Horizontally-disposed product illumination assembly 200 and a corresponding horizontally-disposed background assembly 300 are positioned in opposition sufficiently distant to ensure product being directed from conveyor 14, in particular by slide 12, passes therethrough without interference. A detector 400 is positioned to image product passing between product illumination assembly 200 and background assembly 300. Detector 400 has a vertical field of vision. The point at which product passes between product illumination assembly 200 and background assembly 300 is identified as scan line 700. Scan line 700 is of sufficient height to image passing product. To the extent product is less than the height of the scan line 700, detector 400 images background surface 302, which is aligned with detector 400 and scan line 700. Detector 400 images scan line 700 through product illumination assembly 200 via viewport 202. To increase the effectiveness of detector 400, product is illuminated at scan line 700. To reduce contrast between acceptable product reflecting illumination from product illumination assembly 200, background surface 302 is illuminated from within background assembly 300 consistent with the wavelength, or wavelengths, and intensity, or intensities, of product illumination assembly 200. Background surface 302 is of sufficient height and position to include the arc or chord length of the field of vision of detector 400 passing through viewport 202 and scanline 700 at the inner surface 303 of background assembly 300. One or more ejectors 500, each having a plurality of ejector nozzles, are positioned adjacent illumination device 100 to deflect selected product from trajectory 32. When a product passing through scan line 700 is identified by detector 400 as having the characteristic to be separated from the remaining product, the appropriate nozzle of ejector 500 is activated at the approximate time the product will pass the particular nozzle of ejector 500.

It is preferred that product be as completely imaged, particularly both front and back, as possible for sorting. To that extent, in the preferred embodiment, background assembly 300 is integrated into product illumination assembly 200, as depicted as background assembly 600 in FIG. 4, and two product illumination assemblies 200 are utilized.

Depending on the product to be sorted and the characteristic or characteristics selected as the basis for sorting, a particular wavelength, or wavelengths, and intensity, or intensities, of light may be desirable for characteristic identification. Problematically, a change in product or in characteristic for sorting may require a change in wavelengths and intensities. In conventional product sorting machines, such a change may require replacement of the existing illumination assembly.

As depicted in FIGS. 3-7, each product illumination assembly 200 includes a first semiconductor-light-source product-illuminating array 204 of semiconductor light sources 208, and a second semiconductor-light-source product-illuminating array 206 of semiconductor light sources 208. Semiconductor light sources include lighting emitting diodes (LEDs), laser diodes, organic LEDs, and any other semiconductor light source. Semiconductor light source refers to lighting devices that utilize semiconductors as a light source and not necessarily the semiconductor itself. First semiconductor-light-source product-illuminating array 204 and second semiconductor-light-source product-illuminating array 206 are positioned sufficiently distant scan line 700 to ensure the light of each semiconductor light source of first semiconductor-light-source product-illuminating array 204 and second semiconductor-light-source product-illuminating array 206 sufficiently blend to provide uniform illumination of scan line 700. In the preferred embodiment, first semiconductor-light-source product-illuminating array 204 and second semiconductor-light-source product-illuminating array 206 are affixed on supports 210. Supports 210 are angled to ensure the greatest illuminance of scan line 700 from first semiconductor-light-source product-illuminating array 204 and second semiconductor-light-source product-illuminating array 206. Illuminance is the total amount of visible light illuminating (incident upon) a point on a surface from all directions above the surface. This "surface" can be a physical surface or an imaginary plane. Supports 210 must be sufficiently located so as not interfere with detector 400.

Likewise, as depicted in FIG. 3 with respect to background assembly 300, and in FIGS. 4-7 with respect to background assembly 600 at least a single semiconductor light source background illuminating array 604 of semiconductor light sources 208, which may be light-emitting diodes. Semiconductor light source background illuminating array 604 is positioned sufficiently distant background 302 to ensure the light of each semiconductor light source of the semiconductor light source background illuminating array 604 sufficiently blends to provide uniform illumination of background 302. In the preferred embodiment, semiconductor light source background illuminating array 604 is affixed on support 610. Support 610 is angled to ensure the illuminance of background 302 consistent with scan line 700 from semiconductor light source background illuminating array 604. Support 610 must be sufficiently located so as not interfere with detector 400. A second array of semiconductor light sources may be located opposite semiconductor light source background illuminating array 604.

Alternatively, supports 210 may be altered such that each semiconductor light source array may be relocated within illumination device 100 and the light from each array redirected, by prisms or mirrors, to properly illuminate scan line 700 and background 302 (not shown). Various methods to redirect light and to encourage blending of light sources are well known in the art.

In operation, each detector 400 is located above the horizontal centerline of illumination device 100, views scan line 700 approximately at the center of illumination device 100, and views background 302 below the horizontal centerline 800. The wavelength(s) and intensity(ies) impinging product at scan line 700 from first semiconductor-light-source product-illuminating array 204 and second semiconductor-light-source product-illuminating array 206 are replicated on background 302 by semiconductor light source background illuminating array 604 to provide maximum contrast of characteristics on passing product for identification by detector 400 and therefore activation of ejector 500.

First semiconductor-light-source product-illuminating array 204 is composed of a series of semiconductor light sources 208, which may be of one or more colors. In circumstances where semiconductor light sources 208 in first semiconductor-light-source product-illuminating array 204 are of a plurality of wavelengths, semiconductor light sources 208 cycle through the same sequence of color throughout the array. Repetition of color ensures that the resulting wavelengths blend by the time the light reaches scanline 700. Likewise, in circumstances where semiconductor light sources 208 of a plurality of wavelengths are arrayed on first semiconductor-light-source product-illuminating array 204, a corresponding array of semiconductor light sources 208 are fixed for second product-illuminating array 206 in a complementary sequence. For example, a sequence of red and green semiconductor light sources 208 in first semiconductor-light-source product-illuminating array 204 would be complemented by a sequence of green and red semiconductor light sources 208 in second semiconductor-light-source product-illuminating array 204. In the preferred embodiment, first semiconductor-light-sources product-illuminating array 204 is of a single color, such as red, and second semiconductor-light-source product-illuminating array 206 is of a single color, such as blue. Use of a consistent color semiconductor light sources 208 per first and second array is preferred for ease of repair and manufacture. The number of colors permissible in the assembly is a result of the density of semiconductor light sources and distance from scanline 700 or background 302.

Background array 604 complements both first semiconductor-light-sources product-illuminating array 204 and second semiconductor-light-sources product-illuminating array 204, such that if the color of first semiconductor-light-sources product-illuminating array 204 is red, and the color of second semiconductor-light-sources product-illuminating array 206 is blue, background array 604 will constitute a combination of red and blue semiconductor light sources.

Further, the illuminance on passing product and the background 302 may be controlled by adjusting the intensity of semiconductor light sources 208 contained in first semiconductor-light-source product-illuminating array 204, second semiconductor-light-source product-illuminating array 206 and background array 604. The intensity of each semiconductor light source 208 may be independently controlled to affect the intensity of the wavelength(s) emitted. Such control may be via a computer or other device known in the art. Any variance in emitted intensity of any particular semiconductor light source 208 may be controlled to ensure consistent intensity. Similarly, the intensity of all semiconductor light sources 208 of a particular wavelength or wavelengths found in first semiconductor-light-source product-illuminating array 204, second semiconductor-light-source product-illuminating array 206 and background array 604 may be commonly controlled and adjusted.

Illumination device 100 may be positioned perpendicular to trajectory 32 of passing product, regardless of the trajectory's plane. Additionally, product illumination assembly 100, whether incorporating background assembly 600 or mating with background assembly 300, may be fitted with heat sinks 900. Likewise, if background assembly 300 is used, it too may be fitted with heat sinks 950. In operation, the heat from semiconductor light sources 208 may be removed from illumination device 100 via such heat sinks. Viewport 202 may be an opening, to additionally permit heat to exit, or may be sealed. The assemblies of product illumination assembly 100, whether incorporating background assembly 600 or mating with background assembly 300, may be sealed against passing product, preventing any contaminants from interfering with semiconductor light sources 208 or background 302. Alternatively background assembly 300 may be the lower of the two assemblies and may contain orifices (not shown) through which passing product not following trajectory 32 and instead falling to into background assembly 300 may exit.

By constructing product illumination assembly 200, and, if applicable, background assembly 300, as a single component, the component may be removed for service or replacement, rather than requiring removal of the individual assemblies. Such modular construction reduces the time required for repair or replacement and therefore increases productivity of the sorting machine.

Construction of illumination assembly 200, and, if applicable, background assembly 300, with illumination from light sources onto scanline 700 and background 302, also eliminates the need for internal reflective surfaces.

Use of semiconductor light sources sufficiently distant scanline 700 and background 302 likewise eliminates the need for any diffuser, thereby reducing the number of parts necessary to illuminate scanline 700 and background 302.

To further improve uniformity of illumination, illumination device 100 may be constructed longer than the width of conveyer 14, or slide 12 if applicable. Thus, the effective area of illumination extends to the full edge of the conveyor 14, or slide 12.

Figure 4:
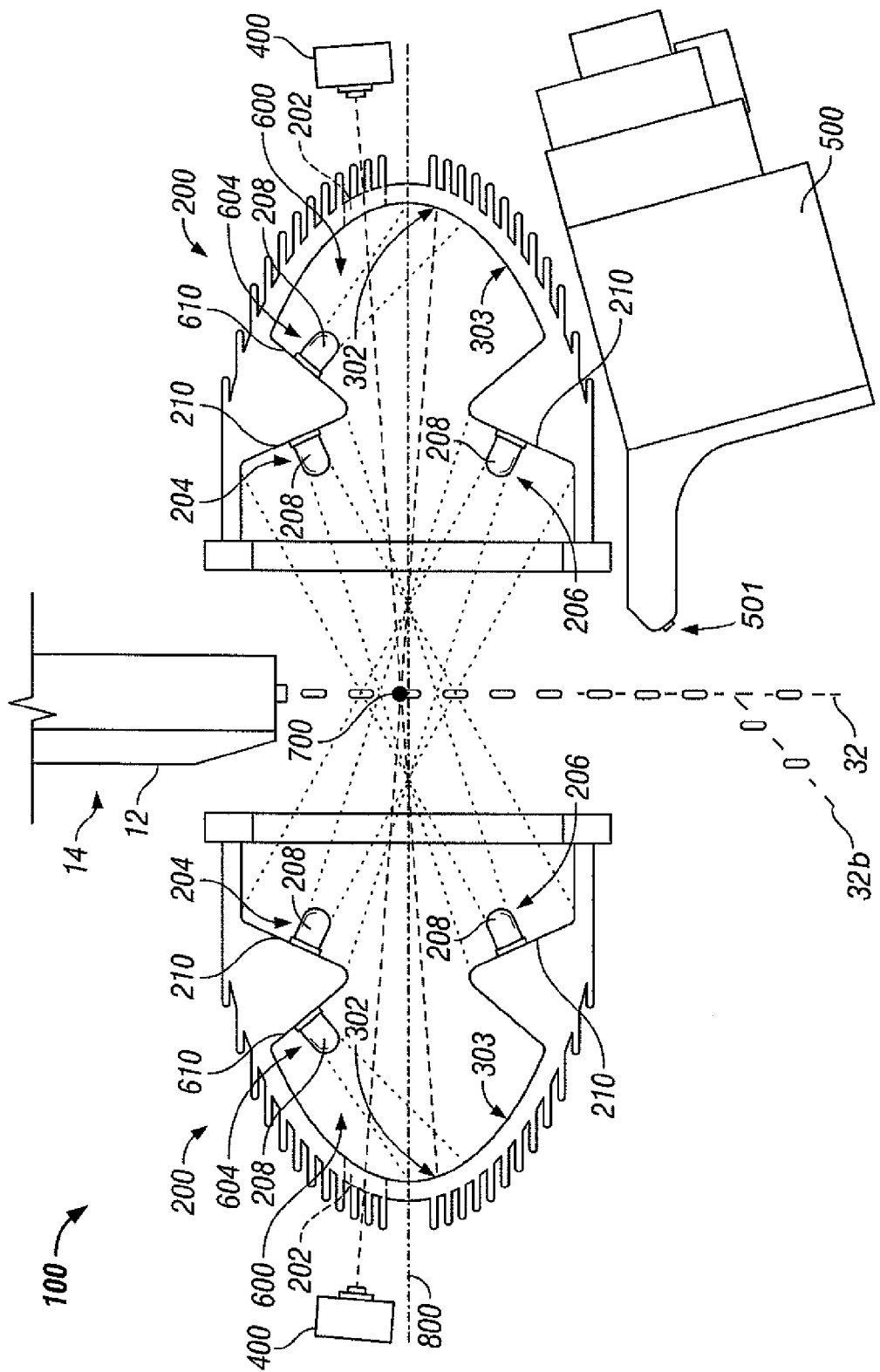
FIG. 4 depicts a cross-sectional view of the illumination device of the preferred embodiment of the present invention.
Figure 5:
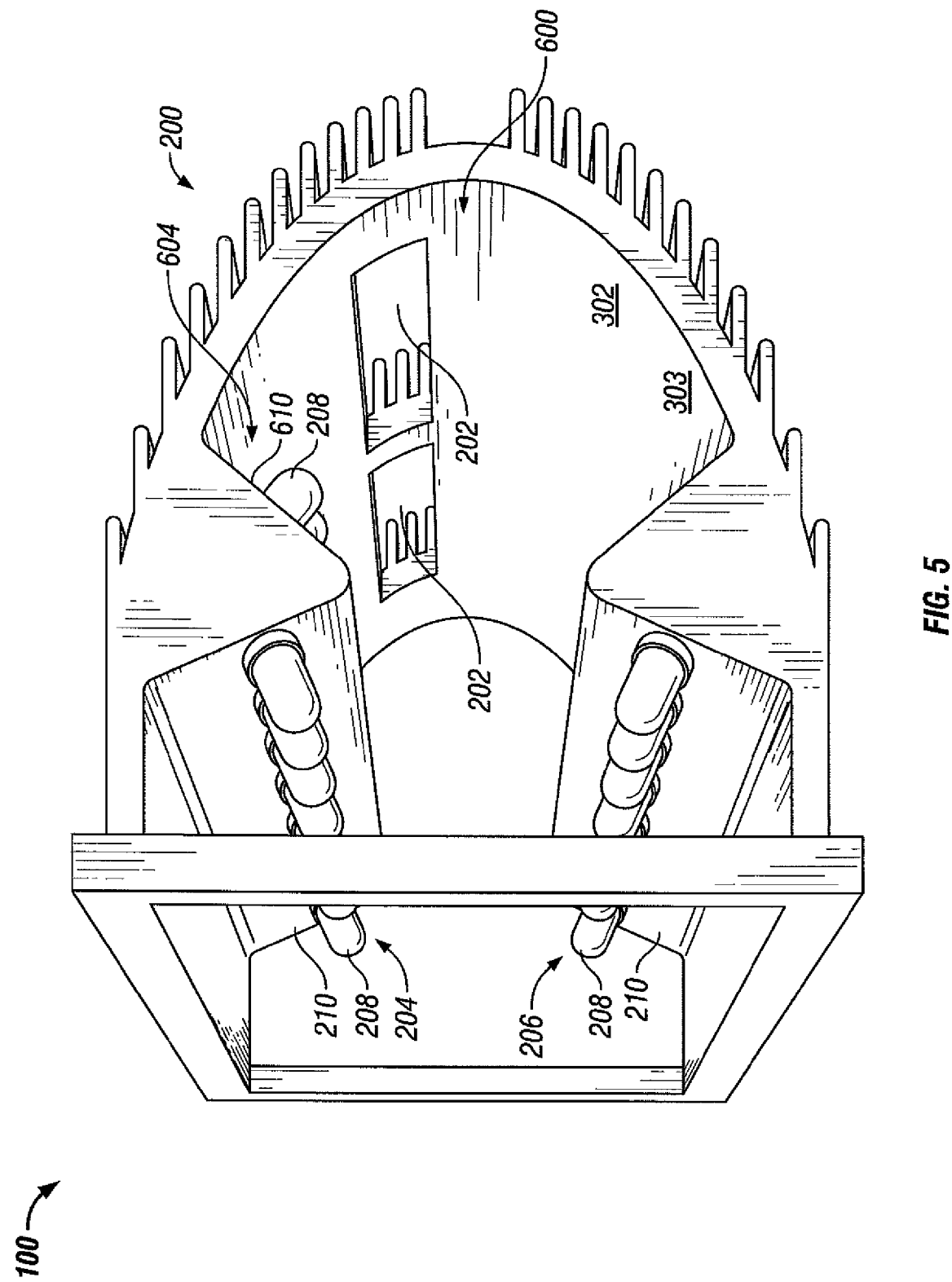
FIG. 5 depicts a perspective view of a section of one half of the illumination device of the preferred embodiment of the present invention.
Figure 6:
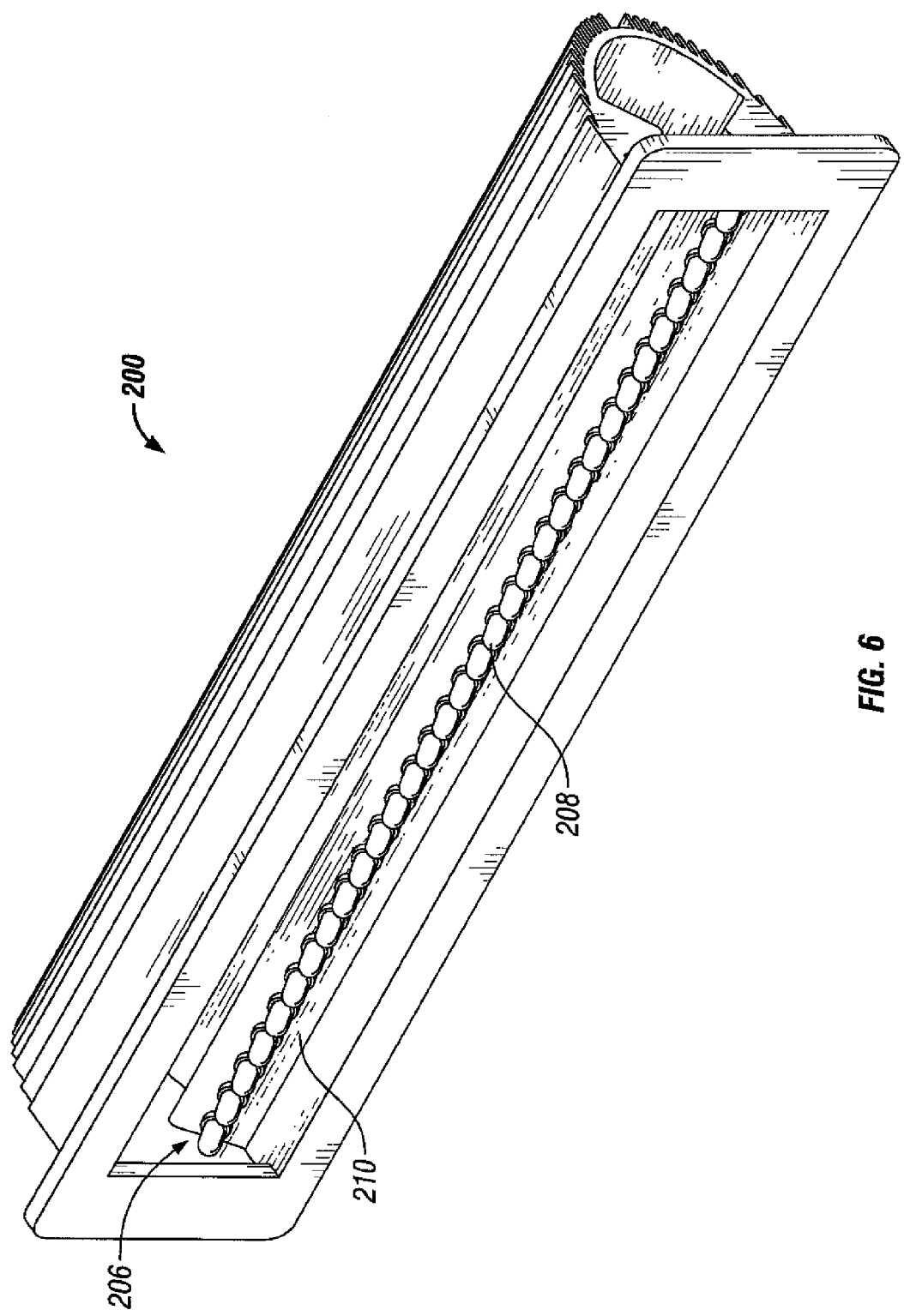
FIG. 6 depicts a perspective view of an entire one half of the illumination device of the preferred embodiment of the present invention.
Figure 7:
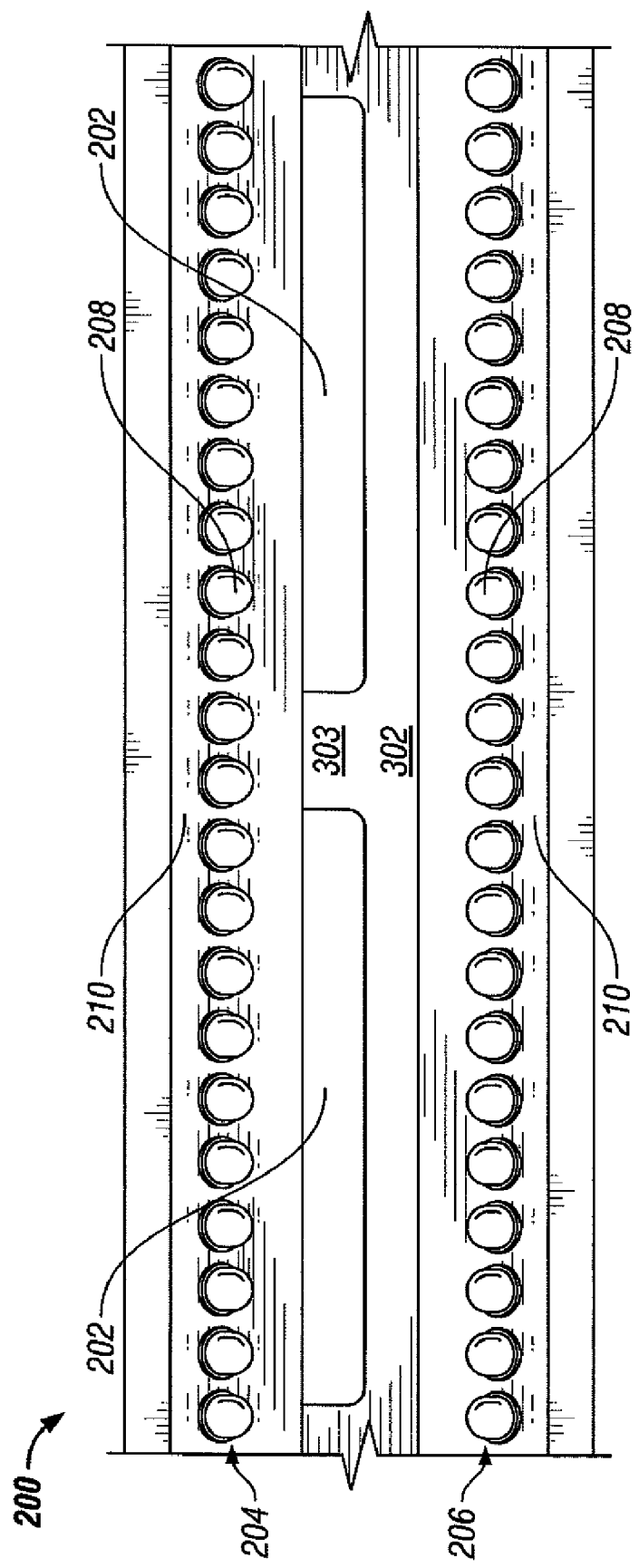
FIG. 7 depicts the front of one half of the illumination device of the preferred embodiment.
Figure 8:
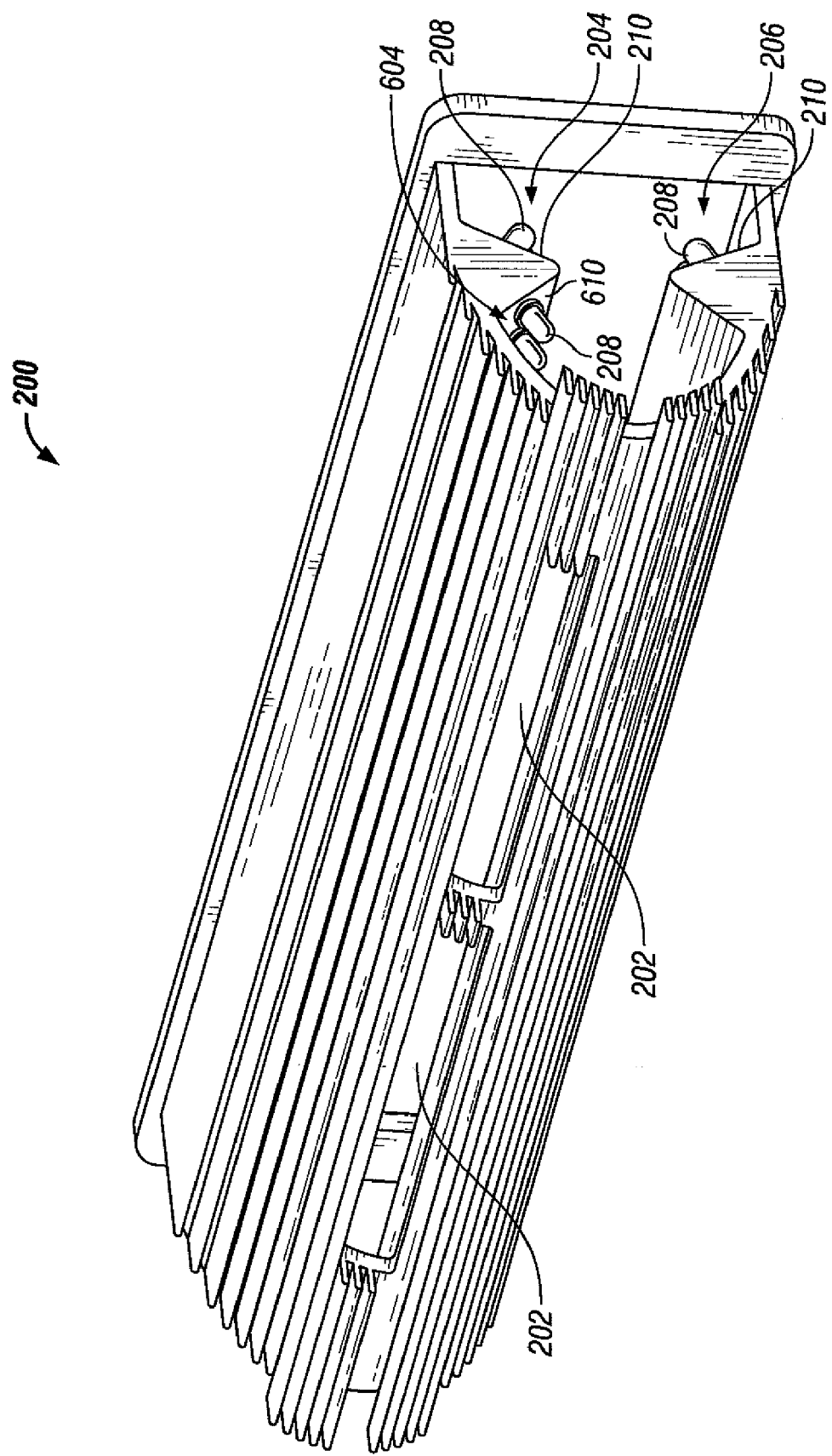
FIG. 8 depicts a perspective view of the rear of one half of the illumination device of the preferred embodiment of the present invention.

Referring to FIGS. 3 and 4, ejector 500 comprises a series of nozzles 501 for selective intermittent ejection of compressed gas, fluid or air (not shown) into trajectory 32. Nozzles 501 are aligned parallel to scanline 700 adjacent trajectory 32, such that any individual product (not shown) identified to be sorted may be diverted to trajectory 32b without diverting adjacent product.

In operation, upon flow of a quantity of products along trajectory 32 through vision system 10, detector 400 outputs optical data in relation to a product passing along scan line 700 and transmits such data to a processor for determination whether the acquired data is within a range of acceptable levels or outside such range. If the data is not within specific parameters, the particular nozzle or nozzles 501 of ejector 500 associated with the lateral position of the identified product is engaged to impart a force to the particular item as it passes, thereby changing the trajectory of the identified product. For illustration purposes, the trajectory of a rejected product is depicted as 32b and the trajectory of a product that is not rejected is depicted as 32.

The machine vision system 10 of the present invention is useful in a variety of applications to identify measuring characteristics of a product. The high and relatively even intensity of illumination within illumination device 100 at scanline 700 makes the present invention particularly useful in identifying flaws in transparent products, such as plastic pellets.

In an application involving a transparent product such as a plastic pellet, a characteristic to be scanned, and upon which sorting is conducted, is the existence of contaminants in the product. Transparent products involve a lensing effect wherein light variations exterior to the product may be reflected by the product. The present invention minimizes such lensing effect in part by limiting the light impinging on product and by controlling the one or more specific wavelengths and intensities detected for processing. Additionally, the plurality of semiconductor light source arrays within illumination device 100 ensures uniform wavelengths and intensities of light at scanline 700 and at background 302 for comparison purposes.

Additionally, an opaque contaminant may be identified using the illumination device 100 of the present invention. A method of determining an opaque contaminant is to determine the deviation of the total quantity of light intensity as measured at detector 400 as the product passes through scanline 700. An opaque contaminant reflects less light to detector 400 than a product that contains no contaminant. The illumination device 100 of the present invention produces illumination levels at scanline 700 that are not distorted by shadows created by uneven lighting and surface imperfections of the product to be scanned and sorted.

The foregoing disclosure and description of the invention is illustrative and explanatory thereof. Various changes in the details of the illustrated process may be made within the scope of the appended claims without departing from the spirit of the invention. The present invention should only be limited by the following claims and their legal equivalents.

I claim:

1. An illumination device for use with a product inspection machine,
    said illumination device having a first edge and a second edge;
    said product inspection machine configured to inspect products according to at least one characteristic,
    said product inspection machine used in conjunction with a product conveyor,
        said product conveyor positioned to direct said products from said first edge of said illumination device to said second edge of said illumination device,
    said product inspection machine having at least one photodetector,
        said photodetector having a vertical field of vision,
    said illumination device comprising:
    at least one horizontally-disposed product illumination assembly,
        said at least one horizontally-disposed product illumination assembly having a front side and a rear side,
        said at least one horizontally-disposed product illumination assembly having a horizontally disposed first array of semiconductor light sources,
            said first array of semiconductor light sources having a repeated sequence of at least one wavelength of semiconductor light sources,
                said first array of semiconductor light sources positioned to illuminate a scanline beyond said front side of said at least one horizontally-disposed product illumination assembly,
        said at least one horizontally-disposed product illumination assembly having a horizontally disposed second array of semiconductor light sources,
            said second array of semiconductor light sources having a repeated sequence of at least one wavelength of semiconductor light sources,
                said second array of semiconductor light sources positioned to illuminate said scanline beyond said front side of said at least one horizontally-disposed product illumination assembly,
        said at least one horizontally-disposed product illumination assembly having a viewport therethrough at said rear side of said at least one horizontally-disposed product illumination assembly,
    at least one of said at least one photodetectors positioned to imagine said products at said scanline through said viewport,
    at least one horizontally-disposed background assembly,
        said at least one horizontally-disposed background assembly sufficiently distant,
        said at least one horizontally-disposed product illumination assembly to permit said products to pass therethrough,
        said at least one horizontally-disposed background assembly having an inner surface,
            said inner surface of said at least one horizontally-disposed background assembly having a background surface aligned with said viewport and said scanline,
                said background surface having height at least equal to said vertical field of vision of said photodetector at said inner surface,
        said at least one horizontally-disposed background assembly having at least one horizontally disposed background array of semiconductor light sources,
            said background array of semiconductor light sources having a repeated sequence of at least one wavelength of semiconductor light sources,
                said repeated sequence of at least one wavelength of semiconductor light sources identical in wavelength emission to the combination of said first array of semiconductor light sources and said second array of semiconductor light sources, and said background array of semiconductor light sources positioned to illuminate said background surface.

2. The illumination device of claim 1, wherein the intensity of the semiconductor light sources of at least one of said at least one wavelength of semiconductor light sources in said first array of semiconductor light sources and in said second array of semiconductor light sources and in said background array of semiconductor light sources is instantaneously adjustable.

3. The illumination device of claim 2, wherein said semiconductor light sources are light-emitting diodes.

4. The illumination device of claim 3, wherein:
    the width of said at least one horizontally-disposed background assembly is equivalent to the width of at least one horizontally-disposed product illumination assembly,
    one of said at least one horizontally-disposed background assembly is contained within each of said at least one horizontally-disposed product illumination assembly and two of said at least one horizontally-disposed product illumination assembly are oppositely positioned.

5. The illumination device of claim 4, wherein:
    said product conveyor has width,
    the width of said at least one horizontally-disposed product illumination assembly is greater than said width of said product conveyor.

6. The illumination device of claim 5, wherein said product inspection machine is a machine vision sorting machine.

7. The illumination device of claim 4, wherein said product inspection machine is a machine vision sorting machine.

8. An illumination device for use with a product inspection machine, comprising:
    at least one horizontally-disposed product illumination assembly,
        said at least one horizontally-disposed product illumination assembly having a front side and a rear side,
        said at least one horizontally-disposed product illumination assembly having a horizontally disposed first array of semiconductor light sources,
            said first array of semiconductor light sources having a repeated sequence of at least one wavelength of semiconductor light sources,
                said first array of semiconductor light sources positioned to illuminate a scanline beyond said front side of said at least one horizontally-disposed product illumination assembly,
the intensity of the semiconductor light sources of at least one wavelength of said at least one wavelength of semiconductor light sources of said first array of semiconductor light sources being instantly controllable,
said at least one horizontally-disposed product illumination assembly having a horizontally disposed second array of semiconductor light sources,
said second array of semiconductor light sources having a repeated sequence of at least one wavelength of semiconductor light sources,
said second array of semiconductor light sources positioned to illuminate said scanline beyond said front side of said at least one horizontally-disposed product illumination assembly,
the intensity of the semiconductor light sources of at least one wavelength of said at least one wavelength of semiconductor light sources of said second array of semiconductor light sources being instantly controllable,
said at least one horizontally-disposed product illumination assembly having a viewport therethrough at said rear side of said at least one horizontally-disposed product illumination assembly,
at least one horizontally-disposed background assembly,
said at least one horizontally-disposed background assembly having an inner surface,
said inner surface of said at least one horizontally-disposed background assembly having a background surface aligned with said viewport and said scanline,
said at least one horizontally-disposed background assembly having at least one horizontally disposed background array of semiconductor light sources,
said background array of semiconductor light sources having a repeated sequence of at least one wavelength of semiconductor light sources,
said repeated sequence of at least one wavelength of semiconductor light sources identical in wavelength emission to the combination of said first array of semiconductor light sources and said second array of semiconductor light sources,
the intensity of the semiconductor light sources of at least one wavelength of said at least one wavelength of semiconductor light sources of said background array of semiconductor light sources being instantly controllable and equivalent to the intensity of the corresponding semiconductor light sources of the same at least one wavelength of said first array of semiconductor light sources and said at least one wavelength of said second array of semiconductor light sources,
said background array of semiconductor light sources positioned to illuminate said background surface.

9. The illumination device of claim 8, wherein said semiconductor light sources are light-emitting diodes.

10. The illumination device of claim 9, wherein said product inspection machine is a machine vision sorting machine.

11. The illumination device of claim 8, wherein said product inspection machine is a machine vision sorting machine.

* * * * *

UNITED STATES PATENT AND TRADEMARK OFFICE
CERTIFICATE OF CORRECTION

PATENT NO. : 7,339,660 B1 Page 1 of 1
APPLICATION NO. : 11/564622
DATED : March 4, 2008
INVENTOR(S) : Avi P. Cohn and Larry H. Mack, Jr.

It is certified that error appears in the above-identified patent and that said Letters Patent is hereby corrected as shown below:

Column 9, line 58, the word "imagine" should read --image--.
Column 9, line 62, the word "distant," should read --distant--.

Signed and Sealed this

Third Day of June, 2008

JON W. DUDAS
*Director of the United States Patent and Trademark Office*